United States Patent [19]
Windisch et al.

[11] Patent Number: 5,110,743
[45] Date of Patent: May 5, 1992

[54] METHOD AND APPARATUS FOR STORING AND MIXING BLOOD SAMPLES

[75] Inventors: Arthur Windisch, Bachenbülach; Heinz Pfenninger, Volketswil, both of Switzerland

[73] Assignee: Oerlikon-Contraves AG, Zurich, Switzerland

[21] Appl. No.: 269,596

[22] Filed: Nov. 10, 1988

[30] Foreign Application Priority Data

Nov. 12, 1987 [CH] Switzerland ............ 04423/87

[51] Int. Cl.$^5$ ............................................ G01N 35/06
[52] U.S. Cl. .................................... 436/48; 422/63; 422/64; 422/67; 422/72; 436/43; 436/45
[58] Field of Search ............ 422/62, 63, 64, 65, 422/67, 72, 73, 100, 104; 436/43, 45, 47, 48

[56] References Cited

U.S. PATENT DOCUMENTS

| | | | |
|---|---|---|---|
| 4,475,411 | 10/1984 | Wellerfors | 422/64 |
| 4,478,095 | 10/1984 | Bradley et al. | 422/64 |
| 4,699,766 | 10/1987 | Yamashita | 422/64 |
| 4,965,049 | 10/1990 | Lillig et al. | 422/64 |

FOREIGN PATENT DOCUMENTS 0061317 9/1982 European Pat. Off. .

Primary Examiner—Robert J. Hill, Jr.
Attorney, Agent, or Firm—Sandler, Greenblum & Bernstein

[57] ABSTRACT

Apparatus for storing and mixing blood samples comprises separate storage and mixing discs for storing and mixing blood samples in containers. The discs are driven independently and are provided with complementary grooves. A loading device loads the containers into the storage disc where they are transported to a transfer device. The transfer device successively transfers the containers into an oppositely situated groove of the mixing disc. The mixing disc mixes the blood samples via rotation thereof, after which the containers are transferred to a blood removal device which rotates each container with its blood sample about the lengthwise axis thereof so that a bar code reading device can read a bar code applied to the container. Blood is then withdrawn from the container and delivered to a blood analyzer, after which the container is ejected from the mixing disc by rotation of the mixing disc.

39 Claims, 9 Drawing Sheets

1

METHOD AND APPARATUS FOR STORING AND MIXING BLOOD SAMPLES

BACKGROUND OF THE INVENTION

The present invention relates to a new and improved method of, and apparatus for, the storage and mixing of blood samples or specimens to enable automatic blood analysis thereof.

When accomplishing automated blood analysis or hemanalysis, it is to be appreciated that after having attained a certain degree of automation, the blood samples must be delivered in an automated fashion to the automatic blood analysis device or blood analyzer. Of course, it must be recognized that blood constitutes an exceedingly delicate substance so that it must be handled with extreme care. Hence, whole blood which is to be analyzed must not be permitted to stand around for a longer period of time, since then the blood may stratify. On the other hand, the blood should not be vigorously agitated or moved, for instance forcefully shaken, since in that case the delicate blood cells can become damaged. Since it is well known in this technology that, in particular, whole blood must be handled with an exceedingly great amount of care or quite protectively, there have been developed appropriate apparatuses, especially apparatuses or devices for the mixing, or even more precisely stated, for the moving of the blood before it is delivered to the blood analyzer. However, as a general rule, neither the blood movement patterns or behavior during mixing of the blood nor the equipment which has been developed for such purpose, are suitable for integration into an automated blood handling and analyzing line or arrangement. This is so because of the existence of the various required transition locations or positions, for instance spanning the location where the blood samples are mixed to the location of taking or drawing of the blood samples. Such transition locations have heretofore been frequently designed at the expense of mechanical compromises in the equipment construction and are neither satisfactory from either the standpoint of speed of operation nor operational integrity or security.

SUMMARY OF THE INVENTION

Therefore with the foregoing in mind it is a primary object of the present invention to provide a new and improved method and apparatus for the storage and mixing of blood samples in a fashion which does not suffer from the aforementioned drawbacks and shortcomings of the prior art constructions.

Another and more specific object of the present invention, is directed to an improved method and apparatus for the storage and mixing of blood samples, wherein the blood samples contained in appropriate containers or vessels are received by the apparatus, adequately maintained ready for subsequent analysis and then properly delivered to the automatic blood analyzer serving for the analysis of the blood samples.

Yet a further significant object of the present invention is directed to an improved construction of an apparatus for the storage and mixing of blood samples, wherein the apparatus is readily adaptable to the operating speed of the automatic blood analyzer or blood analysis device and the operational reliability of the apparatus is not only technically satisfied but also the operational or working procedures or steps of the apparatus are reliably performed, so that there is at least minimized if not actually totally eliminated faulty analysis of the blood samples.

Still a further important object of the present invention, aims at providing an apparatus for the storage and mixing of blood samples and which is designed such that blood samples which are encapsulated in a container or vessel, such as a test-tube like container or vessel, can be reliably processed without the need for opening such container or vessel.

A further notable object of the present invention, is concerned with an improved method and apparatus for the preparation of blood samples in a manner such that analysis of the blood samples can be accomplished reliably and accurately, without the need for coming into contact with the blood of the blood sample and wherein blood samples which must be immediately analyzed can be analyzed under priority conditions.

Now in order to implement these and still further objects of the invention, which will become more readily apparent as the description proceeds, the apparatus for the preparation, and specifically also for the storage and mixing of blood samples for the automatic analysis thereof, among other things, is manifested by the features that there is provided a driven storage disc or disc means for the storage of the containers or vessels housing o filled with the blood samples and a mixing disc or disc means which is driven independently of the storage disc or disc means. The mixing disc or disc means serves for the preparation of the blood samples in the containers or vessels. Moreover, the storage disc and mixing disc are arranged adjacent one another or in juxtaposed relationship and are provided at confronting sides or faces thereof with radially extending, mutually complementary grooves or recesses for the reception of an associated container or vessel filled with the blood sample or specimen Additionally, there is provided a transfer device for the transfer of the containers housing or filled with the blood samples from the storage disc to the mixing disc. There is also advantageously provided a blood removal or extraction device which delivers the extracted blood of the blood samples to a blood analyzer.

As alluded to above, the invention is not only concerned with the aforedescribed apparatus for the preparation, and specifically the storage and mixing of blood samples, but also deals with a method for storing and mixing blood samples. To that end, the method of the present development is manifested, among other things, by the features that containers or vessels which house blood samples filled therein are delivered by a loading device or unit to a storage device where the filled containers with their blood samples are stored and successively brought, as needed, to a transfer location or station where these filled containers are transferred to a mixing device where the blood samples are mixed or moved prior to blood analysis. The storage device and mixing device accomplish their respective storage and mixing operations independently of one another. At the mixing device, a blood removal device successively removes blood from the blood samples of the containers and successively delivers such removed blood samples to a blood analyzer.

BRIEF DESCRIPTION OF THE DRAWINGS

The invention will be better understood and objects other than those set forth above will become apparent when consideration is given to the following detailed description thereof. Such description makes reference to the annexed drawings wherein throughout the various figures of the drawings, there have been generally used the same reference characters to denote the same or analogous components and wherein.

DETAILED DESCRIPTION OF THE PREFERRED EMBODIMENTS

Describing now the drawings, it is to be understood that to simplify the showing thereof, only enough of the construction of the apparatus for the preparation, in particular the storage and mixing of blood samples for enabling automatic blood analysis, and the related structure or equipment has been illustrated therein as is needed to enable one skilled in the art to readily understand the underlying principles and concepts of this invention.

Figure 1:
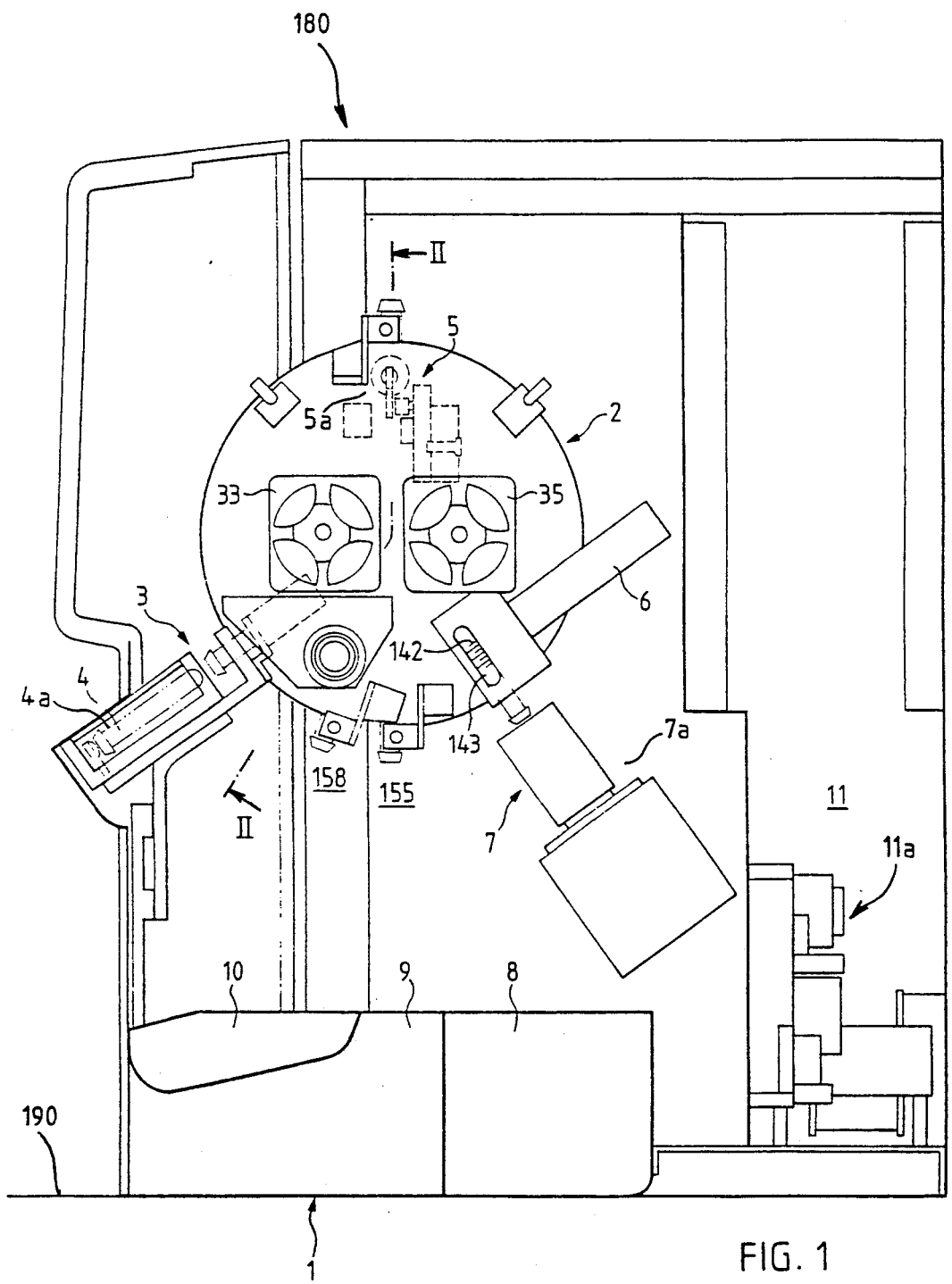
FIG. 1 is a schematic side view of an exemplary embodiment of apparatus for the preparation, and specifically for the storage and mixing of blood samples or specimens and constructed according to the present invention.

Turning attention now specifically to FIG. 1, it will be recognized that the therein depicted exemplary embodiment of blood or blood sample storage and mixing apparatus, generally indicated by reference character 180, comprises a housing 1 of a storage and mixing unit or assembly 2 for blood samples 4 filled into or housed in stoppered containers or vessels 4a, for instances in the form of stoppered test-tube like containers or vessels. There will also be recognized a loading or charging device 3 for the stoppered containers 4a filled with the blood samples 4, a transfer device 5 located at a transfer position or location 5a for transfer of the stoppered containers 4a with their blood samples 4. Additionally, there is provided a code reading device 6, here constituting a bar code reading device for patient-identification of the blood samples 4. At a blood sample removal or extraction location or station 7a, there is located a blood removal or extraction device 7 for the removal of blood from the blood samples 4 contained in the stoppered containers or vessels 4a.

Additionally there will be seen a receiving receptacle or container 8 for receiving stoppered containers or vessels 4a whose blood samples 4 have been properly processed and identified, a further receiving receptacle or container 9 for receiving stoppered containers or vessels 4a containing blood samples 4 which have not been identified, and a still further receiving receptacle or container 10 for receiving stoppered containers or vessels 4a containing so-to-speak emergency-analyzed or emergency-blood samples. There also has been shown in FIG. 1 a compartment or chamber 11 housing the control electronic system or control electronics, generally indicated by reference character 11a, and the related process software for controlling the different functions of the storage and mixing apparatus 180.

The storage and mixing unit or assembly 2 for the blood samples 4, with reference to a support or supporting surface, generally indicated by reference character 190, or as considered with respect to the direction of the force of gravity, can be vertically arranged or parallel to the force of gravity or even arranged at an inclination. A particularly preferably embodiment comprises a vertical arrangement of the storage and mixing apparatus 180 which is oriented in a direction substantially parallel to the force of gravity, whereby the mixing disc or mixing disc means 17 mixes the blood samples overhead. In a modified exemplary embodiment, as also contemplated by the invention and well within the spirit and scope of the teachings thereof, the storage disc or disc means 15 and the mixing disc or disc means 17 can be arranged at an inclination, wherein the blood mixing or moving operation more closely approximates the known design of what is termed "a whole-blood-sample mixer". The just-mentioned inclination can amount to 1° to 89°. Inclination angles which with respect to the vertical amount to between 30° and 60° have been found to be most efficient, and preferably there is proposed an inclination angle of about 45°.

It is, however, here mentioned that a given position or spatial orientation of the storage and mixing unit 2 is not controlling as concerns the teachings and principles of the invention, rather can be freely selected.

Therefore, with that in mind, in the subsequently described exemplary embodiment of storage and mixing apparatus 180 there will be considered a construction where the storage disc 15 and the mixing disc 17 of the storage and mixing unit 2 are arranged in essentially vertical disposition with respect to the associated support or support structure or supporting surface 190, in other words, substantially parallel to the force of gravity. However, as should be understood from what has already been discussed previously, inclined arrangements of the storage and mixing unit 2 also function mechanically in a comparable fashion, so that there need not be undertaken any special constructional measures or modifications as concerns the more essential components or parts of the inventive storage and mixing apparatus 180 should such be dispositioned in inclined orientation, apart, of course, from placing the storage disc 15 and the mixing disc 17 at an inclination. Hence, with an appreciation of such observations, there is no need to specifically describe an embodiment having an inclined disposition of the storage disc 15 and mixing disc 17 and related structure.

Figure 2:
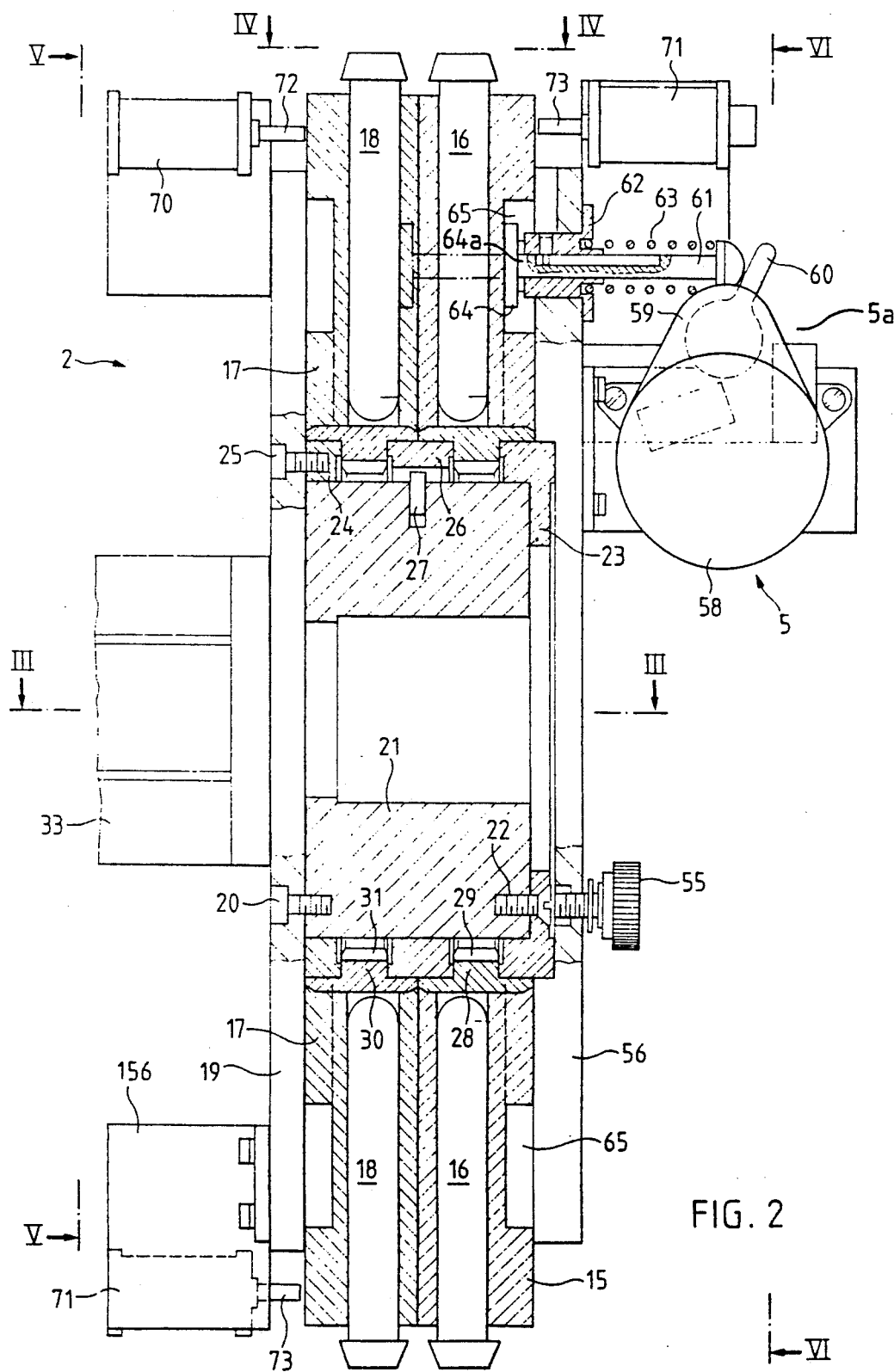
FIG. 2 is a cross-sectional view of the apparatus depicted in FIG. 1, taken generally along the line II—II thereof.

Continuing, as will be recognized by referring to FIG. 2, the storage and mixing unit 2 comprises the aforementioned storage disc 15 for the stoppered containers and their blood samples, generally hereinafter simply referred to as a matter of abbreviation convenience as blood samples 16 when located in the storage disc 15 and the aforementioned mixing disc 17 for the thereto transferred stoppered containers and their blood samples, generally hereinafter simply briefly referred to as blood samples 18 when located in the mixing disc 17. The storage disc 15 and the mixing disc 17 are separately driven in a manner as will be now explained in greater detail. It will be seen that a hub or hub member 21 is secured by means of threaded bolts or screws 20 or equivalent fastening expedients to a substantially circular-shaped plate or plate member 19. By means of threaded bolts or screws 22 or equivalent fastening expedients a ring member or ring 23 is secured to the hub member 21. A further ring member or ring 24 located upon the hub member 21 is secured to the ring member 19 by means of the threaded bolts or screws 25 or the like. Furthermore, the hub member 21 carries a third ring member or ring 26 which is secured against rotation by means of a pin or pin member 27. Upon the ring member 23 and at approximately one half of the ring member 26, there is freely rotatably mounted a gear 28 having an internal toothed rim or toothed crown 29. At the ring member 24 and at approximately the other half of the ring member 26, there is freely rotatable a gear 30 having an inner toothed rim or toothed crown 31.

Figure 3:
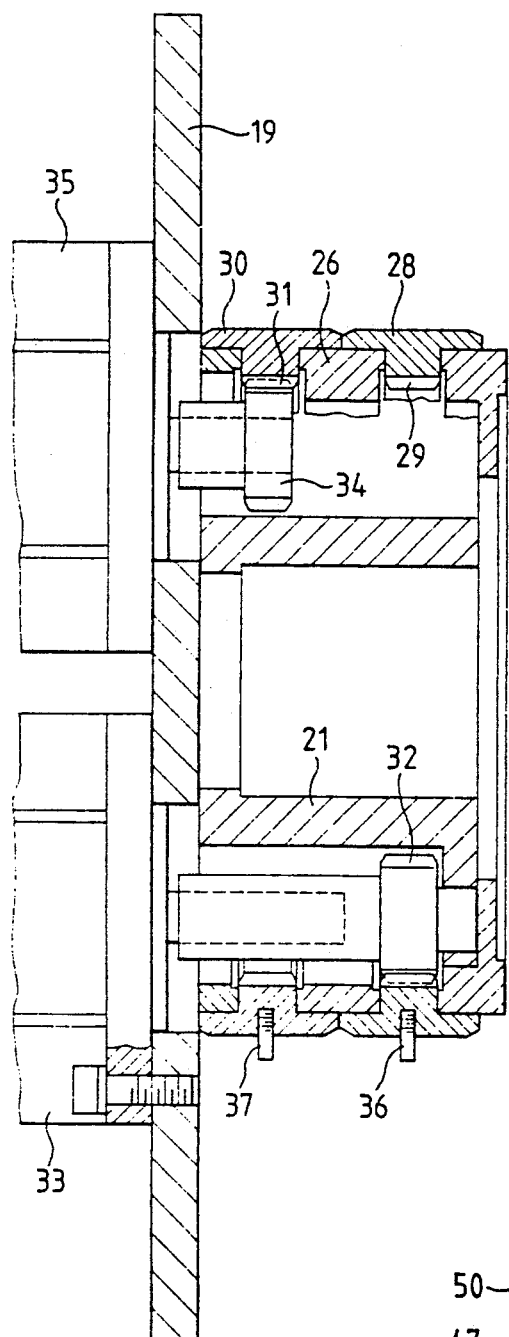
FIG. 3 is a cross-sectional view of the apparatus depicted in FIG. 2, taken substantially along the line III—III thereof.

As best seen by referring to FIG. 3, a drive pinion 32 of a drive motor 33, for instance a stepping motor, meshes with the internal toothed rim 29 of the gear 28. This drive motor 33 is attached to the plate member 91. A drive pinion 34 of a further drive motor 35, likewise attached to the plate member 19, meshes with the internal toothed rim 31 of the gear 30. The storage disc 15 is mounted upon the gear 28 and connected therewith by means of an entrainment member or entrainment means 36. The mixing or mixer disc 17 is mounted upon the gear 30 and is connected therewith by means of an entrainment member or entrainment means 37. Viewed as individual components or parts both of the discs 15 and 17 can be identically constructed.

Figure 4:
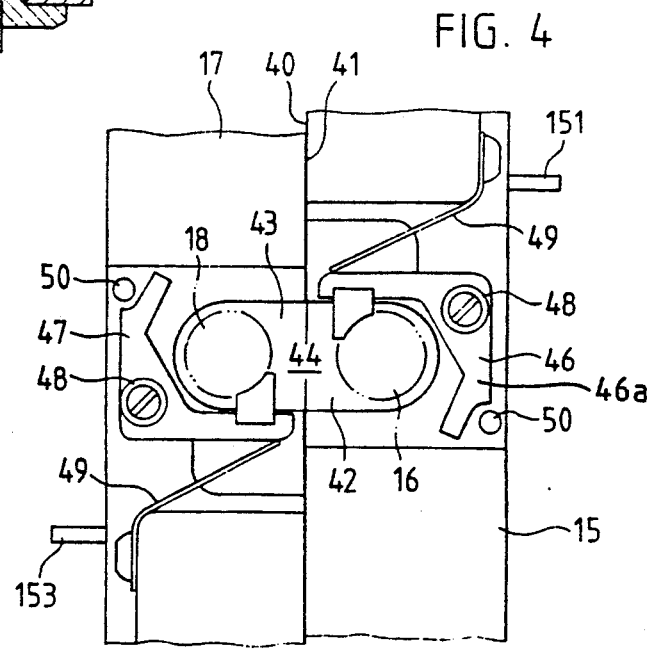
FIG. 4 is a fragmentary top plan view of the apparatus depicted in FIG. 2, taken substantially along the line IV—IV thereof.
Figure 5:
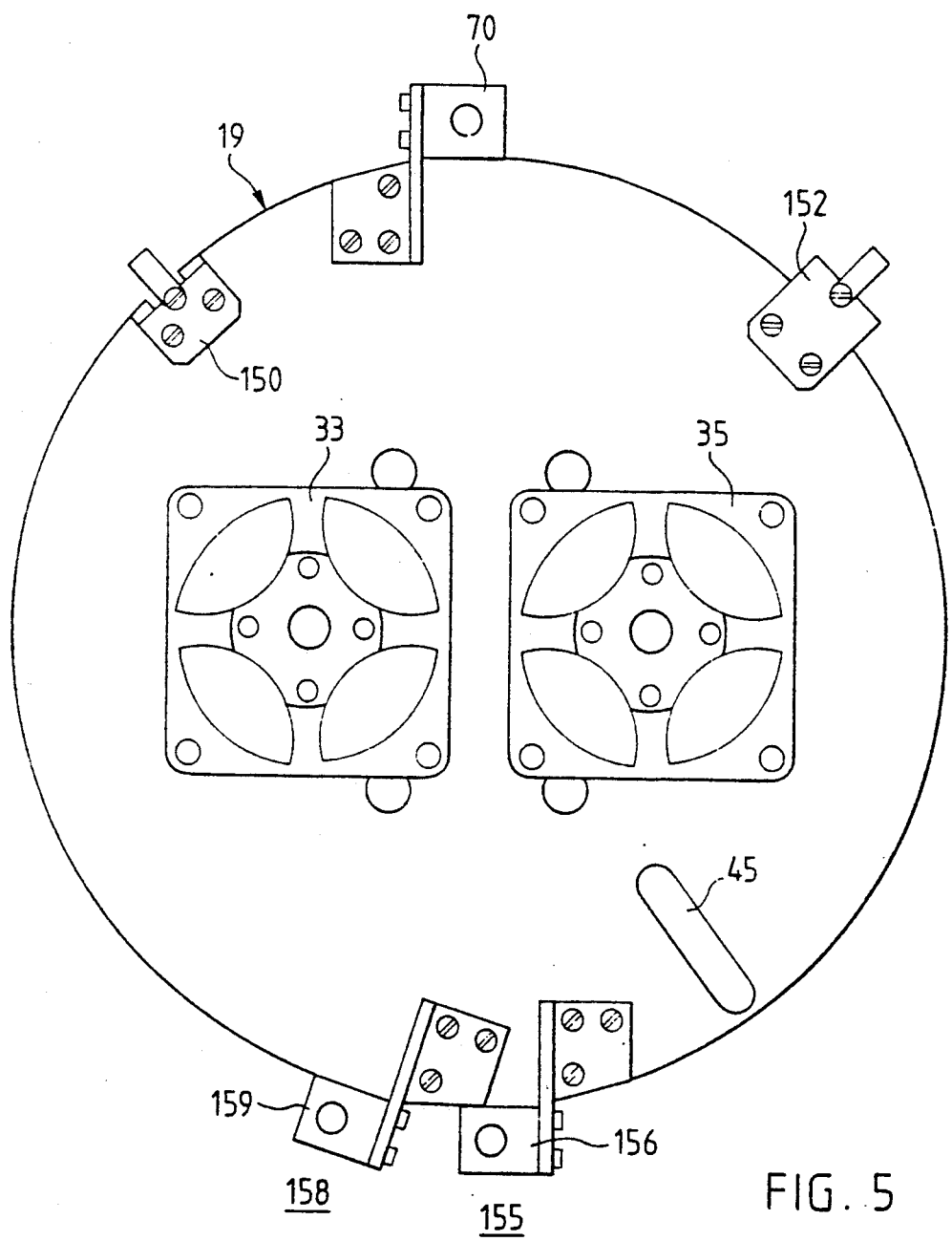
FIG. 5 is an end view of the apparatus depicted in FIG. 2, taken substantially along the line V—V thereof.

Both of these discs, specifically the storage disc 15 and the mixing disc 17, are provided at essentially the same, uniform or equidistant accurate spacing with radially extending mutually confronting grooves or recesses 42 and 43 at the sides or faces 40 and 41 of the storage disc 15 and mixing disc 17 which confront one another, as best seen by referring to FIG. 4. Each two confronting grooves or recesses 42 and 43 compliment one another so as to form a common hollow space or pocket 44 which is open at the circumference or outer surface of each of the discs 15 and 17. Each groove or recess 42 and 43 can receive a blood sample, in the case of the storage disc 15, the blood samples which as previously noted have been conveniently designated by reference numerals 16, and in the case of the mixing disc 17, the blood samples which have been conveniently designated by reference numeral 18. Both of the discs 15 and 17 are provided at that location where there is disposed an associated groove 42 and 43, respectively, with a radial window or viewing opening of approximately the length of the associated groove 42 or 43, as the case may be. By means of an associated window, for instance the window 45 shown in FIG. 5 and provided in the plate member 19, it is thus possible to accomplish an identification of a blood sample 18 located in an associated groove or recess 43 of the mixing disc 17 by means of the bar code reading device 6, and as such will be explained more fully hereinafter.

Reverting again to FIG. 4, it will be recognized that for each groove or recess 42 and 43 of both of the discs 15 and 17 there is provided at the region of the related disc circumference a clamp or clamp member 46 and 47, respectively, serving to fixedly retain each of the blood samples 16 and 18, respectively, which have been placed therein. The clamp member 46 has the shape of a toggle lever 46a and is rotatable about a threaded bolt or screw 48 and is turned or rotated by a leaf or blade spring 49 within the associated groove or recess 42 until this clamp member 46 is prevented by a stop or impact member 50 from accomplishing any further turning or rotation. The other clamp members 47 are constructed in the same manner as the clamp members 46. Both of the discs 15 and 17 are here shown to preferably have the same diameter and are arranged coaxially with respect to one another. However, in this connection it is specifically noted other constructions are readily possible, it being mentioned that there can be used discs of different diameter and having a different number of grooves or recesses and, of course, the discs themselves need not be arranged coaxially with respect to one another. What is important, however, is that at a blood sample transfer location or station, such as the blood sample transfer location 5a of FIG. 1, at both discs, such as the discs 15 and 17 thereof, there is established or maintained a communicating connection for transferring the blood containing containers from the one storage disc, such as the storage disc 15 to the mixing disc, such as the mixing disc 17, and specifically that the grooves or recesses, such as the grooves or recesses 42 and 43 of both discs are located opposite one another at the same moment of time.

By referring now again to FIG. 2 it will be recognized that there is secured by means of rapidly-releasable threaded screws 55 or equivalent structure a plate member 56 upon the ring member 23. This plate member or plate 56 carries the blood sample transfer device 5 located at the blood sample transfer location or position 5a. This transfer device 5 possesses for the driving thereof, for instance a synchronous motor 58. In order to transfer the blood samples, the synchronous motor 58 regularly or periodically drives in counterclockwise direction a crank or crank member 60 by means of a gearing or transmission 59. This crank or crank member 60 acts upon a thrust or pusher rod 61 which can reciprocate to-and-fro in a guide or guide means 62 and is subjected to the outwardly directed pressure or force of a spring or spring member 63. The thrust rod or rod member 61 is provided at the end 64a located opposite the crank 60, with a disc member or disc 64. In the starting position of the crank 60 the disc 64 is located in an annular or ring-shaped groove 65 of the storage disc 15. During each revolution of the crank 60, the disc 64 conveys a blood sample, for instance a blood sample 16, out of the related groove 42 in the storage disc 15 into the oppositely situated empty groove 43 in the mixing disc 17. During such transfer of the blood samples 16, both of the discs 15 and 17 are stationary. Before the transfer of the blood sample 16 can occur, the associated clamp members 46 and 47 must be opened. To that end, there is secured to the plate member 19 located adjacent the mixing disc 17 and the oppositely situated plate member 56 located adjacent the storage disc 15 respective electromagnets 70 and 71 provided with the associated armatures 72 and 73.

Upon energization of these electromagnets 70 and 71 the armatures 72 and 73, respectively, are pressed or urged towards the clamp members 46 and 47, respectively, and rotate these clamp members 46 and 47 against the force of the associated blade or leaf springs 49 away from the blood sample 16. Thus this blood sample 16 can move out of the groove or recess 42 and can be transferred into the oppositely situated groove or recess 43. After transfer of the blood samples 16 in the described manner, the electromagnets 70 and 71 are again de-energized and the clamp members 46 and 47 again close.

Each disc or disc means 15 and 17 fulfills its own function. Specifically, the storage disc 15 serves for the reception of blood samples, initially indicated in FIG. 1 by the blood samples 4, from the loading device or unit 3 and transfers such to the transfer location 5a, and specifically always at such time when there is available a free position in the mixing disc 17. If there is not available such free position in the mixing disc 17 the storage disc 15 preferably is at standstill in order to avoid exposing the whole blood of the blood sample unnecessarily to mechanical loads. On the other hand, the mixing disc or disc means 17 is preferably maintained in motion and has assigned thereto the task of protectively mixing or moving the blood of the blood sample before there is removed or extracted blood for analysis. This mixing disc 17 is brought to standstill only then when a blood sample is extracted or ejected, as still to be explained, or when a blood sample is transferred from the storage disc 15 to the mixing disc 17.

The loading or charging device or unit 3, which as will be recognized by inspecting FIG. 1 is arranged radially with respect to the associated storage disc 15, serves the purpose of conveying or transferring each of the blood samples 4 which have been placed in the loading device or unit 3 by an operator into one of the grooves or recesses 42 of the storage disc 15. As will be seen by referring to FIGS. 7 and 8, a drive motor 80 drives a threaded or transport spindle or spindle member 81 which is rotatably mounted in two bearings 82 and 83 in a frame or frame member 84. A nut or nut member 85 is located upon the threaded spindle 81. The nut member 85 is secured in a clamp or clamp member 86. This clamp member 86 carries a pin 87 which is guided in a groove 88 and a frame member 84 in order to prevent rotation of the nut member 85 upon rotation of the threaded spindle 81. Secured to the clamp member 86 is an entrainment member 89 which is provided with a guide disc or disc member 90.

During such times that a blood sample 4 is not being deposited into the loading device 3 and in order to preclude any possible injury to the operator, this loading device 3 is always then completely closed towards the outside by a substantially cylindrical-shaped screening or closure cap or cap member 91. This screening or closure cap member 91 is rotatably mounted upon a stationary bushing or sleeve member 99 which forms an input chute or blood sample-receiving opening 94. In order to insert a blood sample, it being noted in FIG. 7 a blood sample has been identified by reference numeral 93, the guide disc or disc member 90 is extended by means of the drive motor 80, in other words, is moved away from the storage disc 15. Consequently, there is uncovered the input chute or receiving opening 94 for the insertion of the blood sample 93. During this operation, the inclined edge 91' of the screening or closure cap 91 slides upon an entrainment member 91", whereby such screening or closure cap 91 is opened along the last 10 mm of its movement, due to the force of a pre-biased torsion spring 92. Now the blood sample 93 can be placed into the accessible input chute or receiving opening 94.

Figure 7:
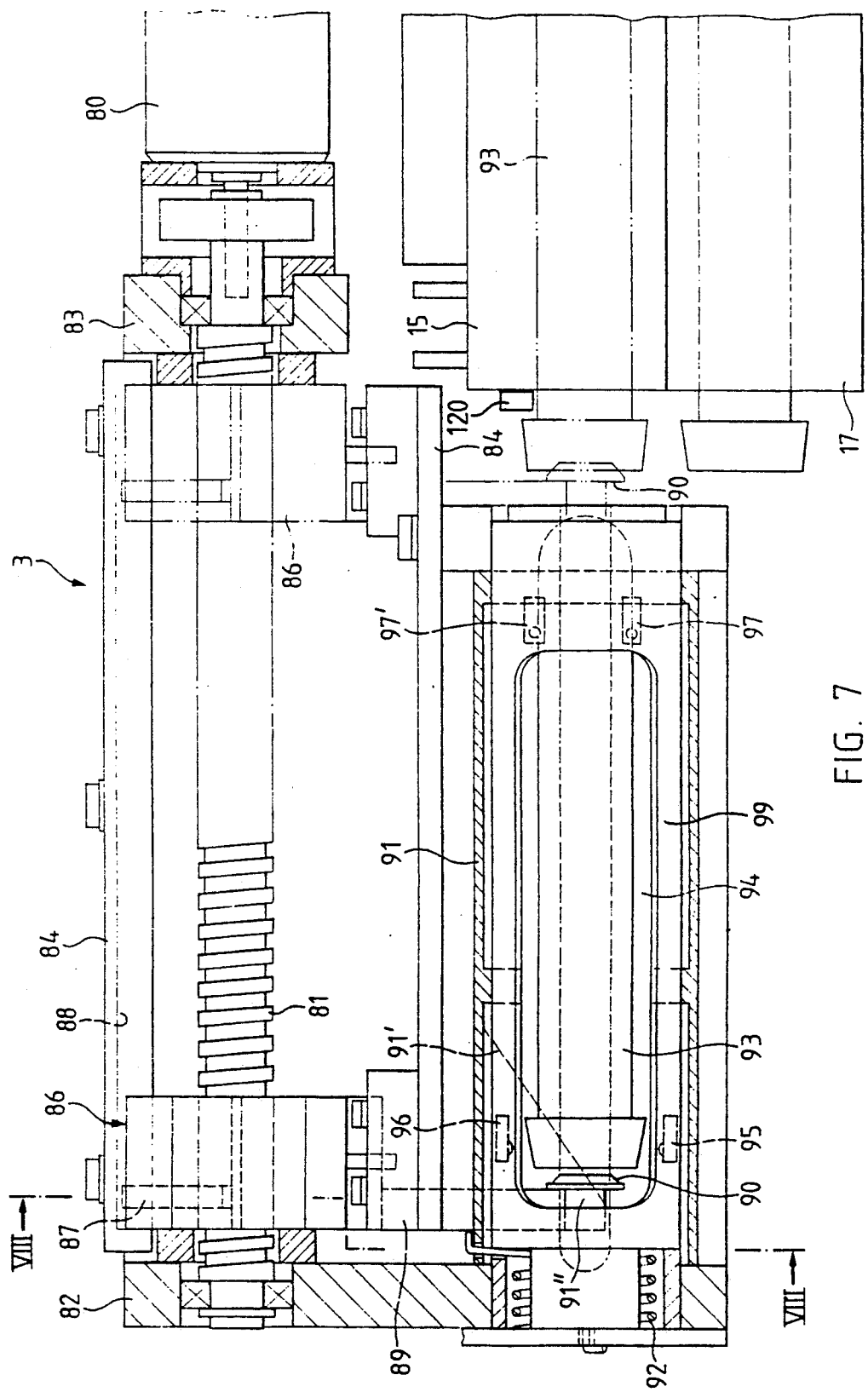
FIG. 7 is an enlarged top plan view of the loading or charging device or unit used in the apparatus depicted in FIG. 1, serving for the loading of the containers or vessels, shown in the form of stoppered test-tube like containers or vessels into the storage and mixing apparatus of FIG. 1.
Figure 8:
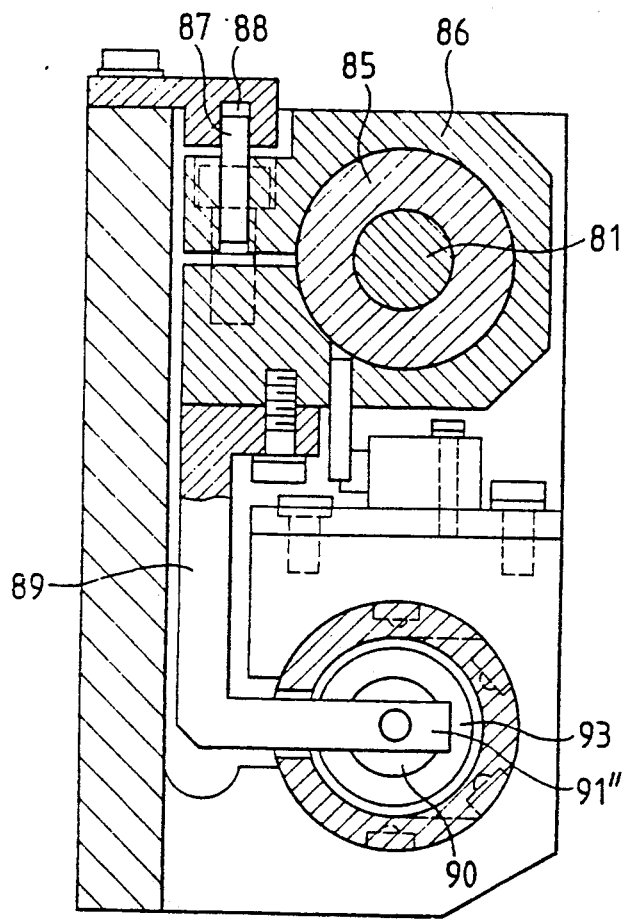
FIG. 8 is a cross-sectional view of the loading device or unit depicted in FIG. 7, taken substantially along the line VIII—VIII thereof.

The presence of a blood sample 93 in the input chute or receiving opening 94 is reported to the electronic control 11a by suitable sensors, here for instance the bifurcated-light barriers or photoelectric detectors 95, 96 and 97, 97' (FIG. 7), whereupon the electronic control 11a undertakes the proper positioning of the storage disc 15. Thereafter, the drive motor 80 for the drive of the threaded spindle 81 is switched-on. This threaded spindle 81 places the nut member 85 into movement and by means of the entrainment member 89 and the guide disc 90 the blood sample 93 is introduced into the corresponding groove or recess 42 (in other words, the receiving opening) of the storage disc 15. During the first 10 mm of the insertion path of the blood sample 93 the screening or closure cap 91 is again closed against the force of the torsion spring 92 by virtue of the coacting action of the inclined edge or ramp 91' and the entrainment member 91". As soon as the blood sample 93 has been completely introduced into the storage disc 15, then a terminal or limit switch, as generally indicated by reference character 120 in FIG. 7, is actuated which by means of the electronic control or control means 11a turns-off the spindle drive motor 80 and turns-on the drive motor 33 for the storage disc 15. The electronic control or control means 11a prevents renewed opening of the input chute or receiving opening 94 when all grooves 42 which are contemplated to be filled with blood samples are occupied by prior introduced blood samples.

Continuing, and as best seen by referring to FIGS. 1, 9 and 10, the blood removal device 7, which is radially arranged at the mixing disc 17 and positioned at the blood removal or extraction or puncturing location 7a, serves to successively remove blood from each one of the blood samples and to successively deliver the sampled blood specimens to a subsequently connected automatic blood analyzer or blood analysis device, generally indicated by reference character 200 in FIG. 9. As has been shown in this FIG. 9 a drive motor 100 drives a drive or operating rod or rod member 105. This drive motor 100 is connected with a gearing or transmission 101 and the output shaft 102 with a crank or crank device 103 which drives by means of the crank pin 104 the drive rod 105. One end 105a of the drive rod 105 is rotatable about a pin or pin member 106 of a clamp or clamp member 107. A needle support or support member or carrier 108 is located in the clamp member 107. This needle support or support member 108 can slide back and forth, in the showing of FIG. 9, can slide up and down, within two bearings 109 and 110 of a housing 111. In a bore or opening 112 provided at the upper end of the needle support 108 there is secured a hollow needle or needle member 114 by means of a clamp or clamp member 113. This hollow needle 114 is provided with an opening or bore 115 in the needle wall 116. The bore or opening 112 in the needle support 108 communicates by means of a hose or line 117 and a two-way valve or valve means 210 with the blood analyzer 200 and also with a source or supply 220 for a flushing or washing agent for flushing or washing the hollow needle 114.

Figure 9:
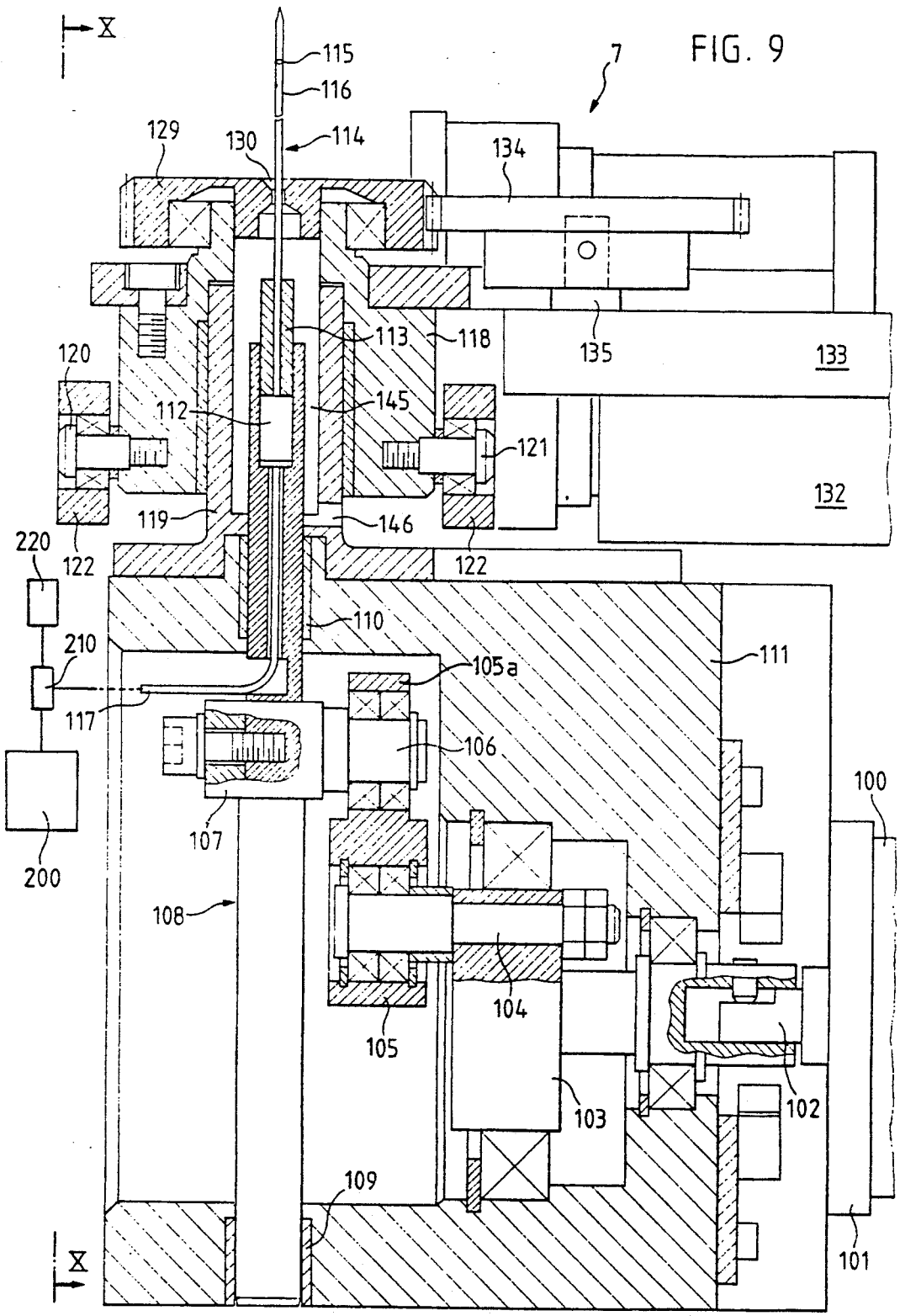
FIG. 9 is a cross-sectional view of the blood or blood sample removal or extraction device used in the storage and mixing apparatus of FIG. 1.

The needle support 108 is concentrically surrounded by an inverted pot-shaped member or pot 118 which can slide back and forth, in the showing of FIG. 9, up and down upon a bearing 119. The pot 118 is carried by a bifurcated or forked member 122 by means of two pins 120 (see FIG. 10) and 121 (see FIG. 9). The one end 122a of the bifurcated or forked member 122 is rotatable about a shaft or axle 123. A free end 124 of the bifurcated member 122, on the one hand, is exposed to the action of the force of a spring or spring member 126 by means of a bolt or bolt member 125 and, on the other hand, such free end 124 of the bifurcated member 122 is subjected to the action of the force of a second drive motor 128 through an eccentric or eccentric member 127 (FIG. 10).

Continuing, it will be observed that a gear 129 is freely rotatably mounted upon the pot or pot member 118. This gear or gear member 129 possesses a central bore or opening 130 to allow throughpassage of the hollow needle 114. A third drive motor 132 drives by means of a gearing or transmission 133 a gear 134 which is seated upon the output shaft 135 of the gearing 133. This gear 134 meshes with the gear 129 which is seated upon the pot or pot member 118.

Figure 10:
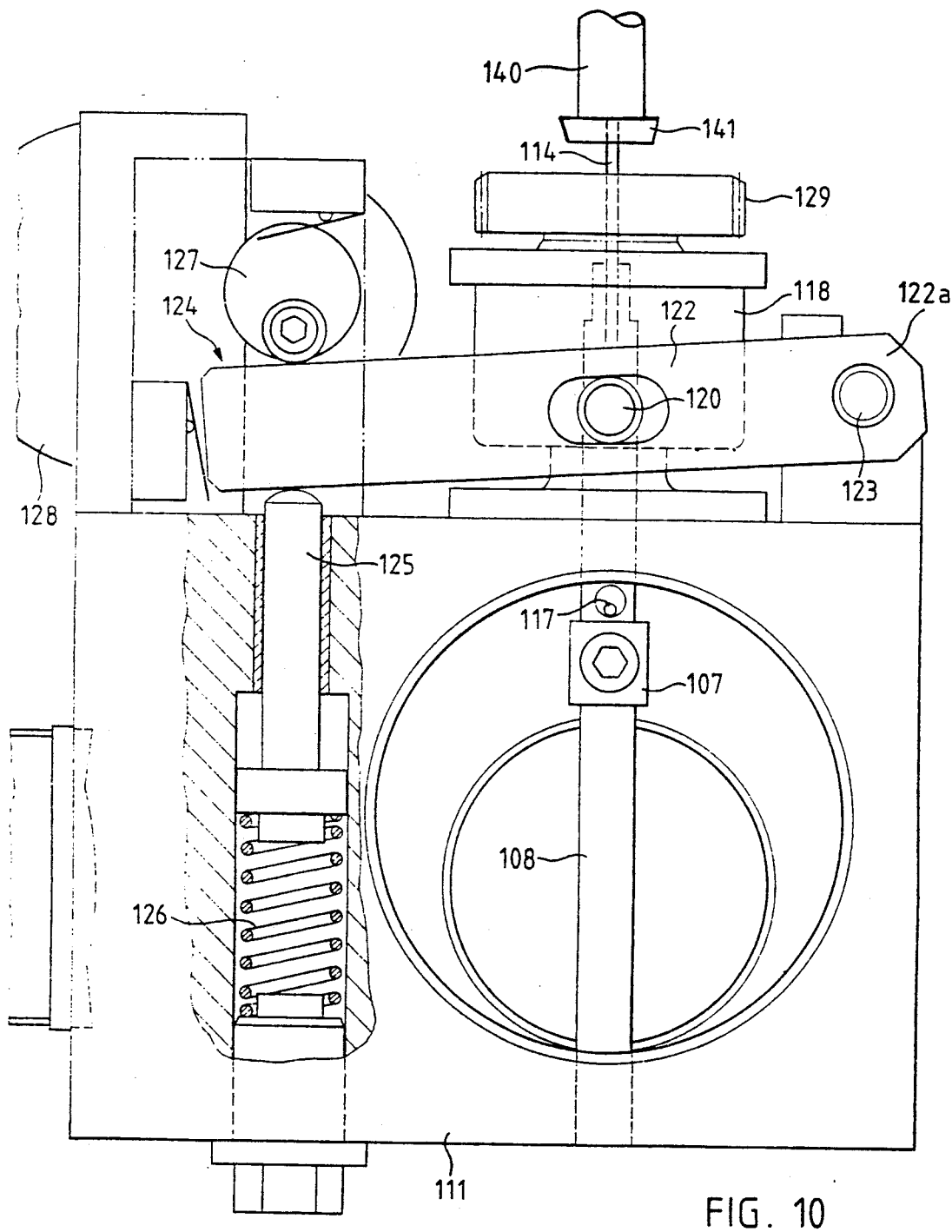
FIG. 10 is an end or front view, partially in cross-section, of the blood removal or extraction device depicted in FIG. 9, taken substantially along the line X—X thereof.

As soon as a blood sample, generally indicated by reference character 140 in FIG. 10, has arrived in front of the blood removal or extraction device 7, then the drive motor 128 is turned-on and the eccentric 127, by virtue of its rotation, enables the spring 126 to lift the bifurcated member 122, so that also the pot 118 together with the gear 129 is raised in the showing of FIG. 10. The gear 129 is then pressed against the stopper or cap 141, here a rubber cap, of the associated blood sample or specimen 140 (stoppered container or vessel housing the blood sample) located in the mixing disc 17, so that there prevails a frictional connection between the gear 129 and the blood sample 140. Thereafter, the drive motor 132 is turned-on and the gear 134 is placed into rotation, which, in turn, drives the gear 129.

Consequently, the blood sample 140 is caused to rotate about its lengthwise axis within the associated groove or recess 43 of the mixing disc 17. The bar code 142 or the like which has been applied to the blood sample 140 thus rotates in front of the window 143 (see FIG. 1) provided in the mixer disc 17. At the same time, the bar code reading device 6 is turned-on and such reading device then determines the identity of the patient corresponding to the blood sample 140. The reason for rotating the blood sample 140 during the reading operation is to ensure that the bar code reading device 6 can properly read the code applied to the blood sample 140 irrespective of its position within the associated groove or recess 43. After reading the bar code 142 the drive motor 132 is turned-off, so that the blood sample 140 comes to standstill. Thereafter, the drive motor 100 is turned-on so that the needle support or carrier 108 is raised in the showing of FIG. 9 and the hollow needle 114 then punctures the pierceable rubber cap or stopper 141 of the blood sample 140. The required quantity of blood is sucked out of the blood sample 140 and delivered by means of the hose or line 117 to the blood analyzer 200. Due to the further rotation of the drive motor 100, the needle support 108 is now downwardly moved, so that the hollow needle 114 is retracted. The drive motor 128 downwardly depresses the bifurcated or forked member 122, so that the gear 129 is released from its prior discussed contact with the blood sample 140. By means of the hose or line 117 there is now conveyed from the flushing agent supply or source 220 the flushing agent into the bore 112 of the needle support 108, which flushing agent then flows through the hollow needle 114 and through the wall opening or bore 115 and into an annular or ring-shaped space or chamber 145 provided in the bearing 119 and such flushing agent then can be removed through an outflow opening or port 146. Now the mixing disc 17 is again turned-on and the next blood sample 140 is rotated until it is positioned in front of the blood removal or extraction device 7.

Having now had the benefit of the foregoing discussion and description of the exemplary embodiment of storage and mixing apparatus 180, its mode of operation will be considered in greater detail and is follows:

A blood sample comprises, for instance, a glass tube or test-tube like container or vessel which initially is evacuated and when removing blood from the patient is filled to a certain desired extent with the patient's blood. This blood sample is then closed by the rubber stopper or cap, such as the rubber cap 141 depicted in FIG. 10. The storage disc 15 and the mixer disc 17 are both driven by their associated drive motors 33 and 35, respectively, so as to rotate in clockwise direction in the illustration of FIG. 1. The blood samples, such as the blood samples identified by reference character 93 in FIG. 7, are individually manually inserted into the loading or charging device or unit 3. In the mixing or mixer disc 17 the blood is protectively mixed or moved due to the rotation of the mixing disc 17. The storage disc 15 can be loaded with blood samples such as the blood samples 16 shown in FIG. 2 independently of the operation of the mixing disc 17. Upon loading of a blood sample, such as the blood sample 93 of FIG. 7, into the loading device or unit 3, the electronic control or control means 11a ensures for the proper positioning of the storage disc 15, and the drive motor 80 for operating the transport or threaded spindle 81 is turned-on so that the blood sample 93 is introduced or conveyed into the storage disc 15. Thereafter, the drive motor 33 for the storage disc 15 is again turned-on at the desired time by the electronic control or control means 11a.

Figure 6:
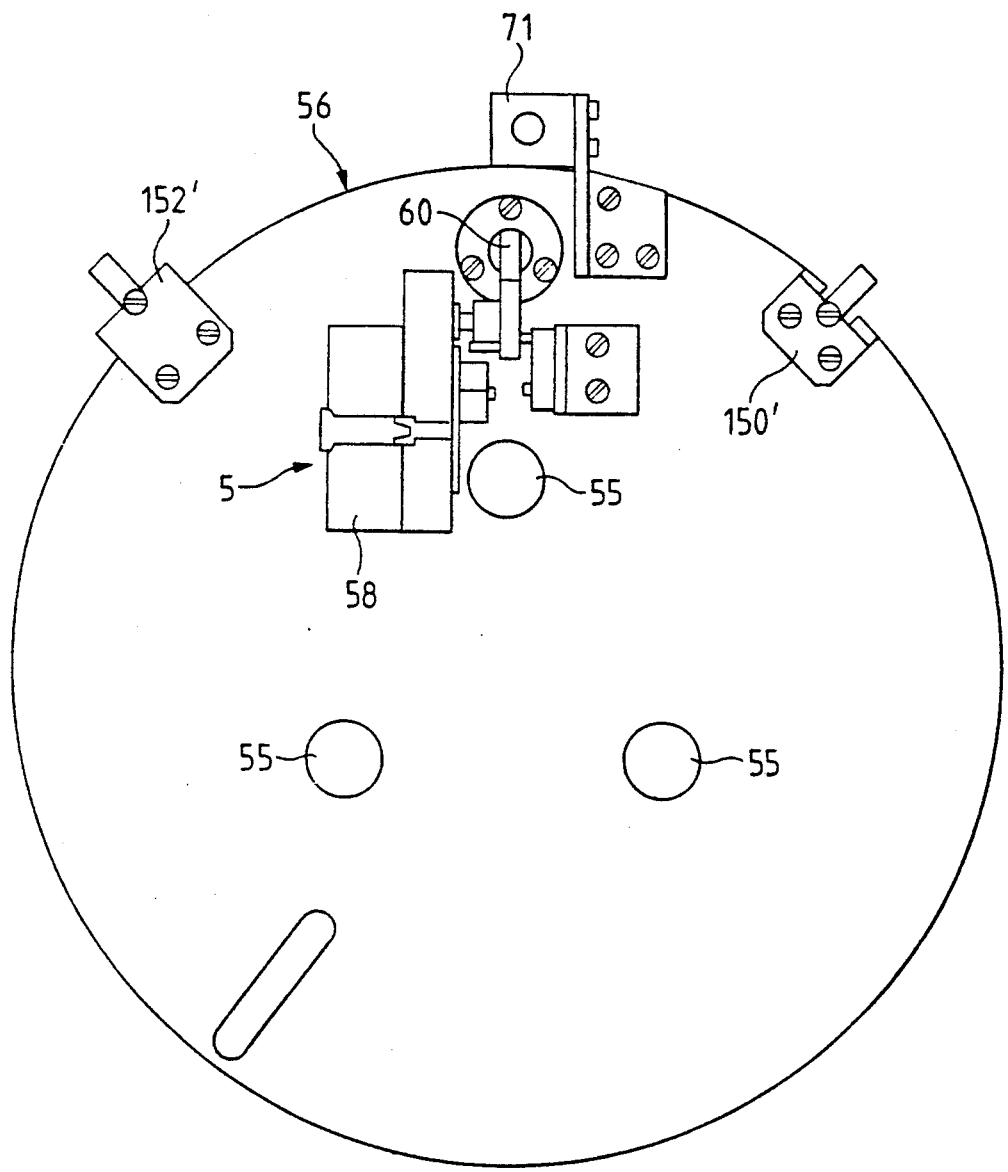
FIG. 6 is an end view of the apparatus depicted in FIG. 2 from the opposite side thereof, taken substantially along the line VI—VI thereof.

Along its path to the transfer device 5, the storage disc 15 passes a bifurcated or forked light barrier or photoelectric detector or sensor 150' which is secured to the plate member 56, as best seen by referring to FIG. 6. As a trigger element there is provided, as shown in FIG. 4, a pin or pin member 151 for each groove or recess 42 and each such pin or pin member 151 is attached to the storage disc 15. Each pin or pin member 151 travels past the light barrier or sensor means 150'. During each such passage the light barrier or sensor means 150' generates a pulse for the electronic control or control means 11a. The electronic and employs them for the control of the operation of the storage disc 15. When the relevant blood sample has reached the transfer device 5 at the blood transfer position or location 5a, the storage disc 15 and the mixing disc 17 are stopped. The electromagnets 70 and 71 or equivalent structure, located at that transfer position 5a, are energized and these energized electromagnets 70 and 71 open the clamps or clamp members 46 and 47 of the associated grooves 42 and 43 of both of the discs 15 and 17. At the same time, the transfer device 5 is turned-on and the related blood sample, such as the upper one of the blood samples 16 appearing in the showing of FIG. 2, is conveyed by the action of the thrust or pusher rod 61 out of the storage disc 15 into the mixing or mixer disc 17, as represented by the there located blood samples 18. Thereafter, the drive motors 33 and 35 for the storage disc 15 and the mixing disc 17 are again turned-on.

As also will be seen by referring to FIG. 6, following the blood sample transfer device 5 the storage disc 15 passes a bifurcated or forked light barrier or sensor means 152' which is secured to the plate member or plate 56. This light barrier 152' is activated during each complete revolution of the storage disc 15. At the mixing disc 17 the bifurcated or forked light barrier 150, which is secured to the associated plate member or plate 19 and which can be triggered by a pin or pin member 153, serves for counting the grooves or recesses 43 at the mixing disc 17. Each groove or recess 43 of the mixing disc 17 is provided with an associated pin or pin member 153 (see FIG. 4). In any event, following the transfer device 5 the mixing disc 17 passes a further bifurcated or forked light barrier or sensor means 152 which is attached to the associated plate member or plate 19. This light barrier 152 is actuated during each complete revolution of the mixing or mixer disc 17.

When the blood sample which is to be analyzed has arrived at the blood removal or extraction position 7a, then the drive motor 35 for the mixing disc 17 is turned-off. There are turned-on the drive motors 128 and 132 which produce a frictional connection with the blood sample, specifically the blood sample 140 of the showing of FIG. 10 and for the rotation of such blood sample 140 about its lengthwise axis. At the same time, and depending upon the mode of operation and construction of the apparatus 180, the bar code reading device or code reader 6, to the extent one is provided is turned-on. This bar code reading device 6 reads any possibly provided bar code 142. When such bar code is not present and the apparatus is operating in the bar code reading mode, then the friction or frictional connection with the blood sample 140 is interrupted and both of the drive motors 128 and 132 are again turned-off. The needle support or carrier 108 is not raised towards the mixing disc 17. The drive motor 36 for the mixing disc 17 is again turned-on. The mixing disc 17 is then further rotated until reaching an ejection or throw-out position 155 (see FIG. 1) and at which position or location the corresponding clamp member or clamp 47 is opened by an electromagnet 156 (see FIG. 2) which is positioned at the region of the ejection position or location 155, so that the blood sample 140 which has not been properly identified can fall out of the associated groove or recess 143. This rejected blood sample 140 is then deposited into the receptacle or container 9 for receiving non-identified blood samples.

On the other hand, if there is present a blood sample 140 which is provided with a bar code 142 and if the bar code reading device 6 is functionally reliable, then the bar code 142 is read and there is carried out patient identification and recordal. Now the bar code reading device 6 is turned-off. The drive motor 132 for rotating the blood sample 140 is likewise turned-off. At this point in time, the drive motor 100 for the needle support 108 raises such needle support 108 towards the blood sample 140 and the hollow needle 114 punctures the rubber cap or stopper 141. There is withdrawn the required quantity of blood from the punctured blood sample 140 and such is then delivered to the blood analyzer 200 where the removed blood sample is analyzed.

After the subsequent return movement of the needle support or carrier 108 there is then operated a not particularly illustrated but conventional displacement switch or switch means which again turns-on the drive motor 35 for the mixing or mixer disc 17 by means of the electronic control or control means 11a. The two-way valve or valve means 210 is switched and the hollow needle 114 is flushed with the flushing agent received from the flushing agent supply or source 220. The mixing disc 17 is further rotated towards the blood sample ejection position or location 155 where the relevant clamping member 47 is opened by the electromagnet 156. The blood sample 140 associated with this clamping member 47, which has now been previously analyzed, slides out of the related groove or recess 43 and is deposited into the receiving receptacle or container 8 for identified blood samples. In the event that the storage and mixing apparatus 180 is designed such that it operates without any bar code reading device 6 then each blood sample 140 in each individual case is evaluated, in other words, each blood sample 140 is punctured, sampled and analyzed.

Now the situation could arise where an emergency occurs so that a given blood sample must be rapidly analyzed while overriding or having priority over the other blood samples. To handle such event, the storage and mixing apparatus 180 is provided with a suitable switch so that the heretofore described normal or standard control can be turned-off and an emergency control turned-on. This emergency operation or emergency blood analysis mode functions as follows:

In the exemplary embodiment under discussion, both in the storage disc 15 as well as in the mixing disc 17, also during normal or standard operation, there is always present a position which is empty, in other words, one of the radial grooves or recesses 42 of the storage disc 15 and one of the radial grooves or recesses 43 of the mixing disc 17 is always left empty or free. In the event that there is required an immediate analysis of an emergency blood sample, then these two empty positions are available and used. To that end, the emergency blood sample, after it has been manually mixed or moved, is introduced into the blood sample loading or charging device or unit 3 from which it is then transported to the storage disc or disc means 15, received in the empty groove or recess 42 of such storage disc 15 and transported without delay to the blood sample transfer location or position 5a and at that location is taken over by the mixing or mixer disc 17. From the transfer position 5a, the emergency blood sample is delivered directly and without any additional mixing rotation of the mixing disc 17, to the blood sample removal or extraction or what also may be termed a puncturing location or station 7a and at that location likewise processed with priority. Thereafter, the emergency blood sample is transferred to an emergency blood sample ejection or discarding position 158 where there is located an electromagnet 159 (see FIG. 5) which opens the related clamping member 47 of the associated groove or recess 43 of the mixing disc 17 and such emergency blood sample is then deposited into the separately provided receiving receptacle or container 10 (see FIG. 1).

In this way, emergency blood samples and so-to-speak routine blood samples are physically segregated from one another at all times. The possibly provided bar code reading device 6 normally remains out of operation during the emergency blood sample analysis, because when an emergency situation arises there is not usually undertaken the normal or standard organizational processing of such blood sample including the application of the bar code or other code thereto as is otherwise possible during routine blood sample analysis.

After there has been completed the processing of the emergency blood sample the again freed position, namely the free groove or recess 42 of the storage disc 15 and the freed groove or recess 43 of the mixing disc 15 are available for handling further emergency blood samples.

By means of the heretofore described storage and mixing apparatus 180 there can be accomplished in random batchwise operation the routine or standard processing or analysis of the blood samples. Since, on the one hand, the storage disc or disc means 15 which is provided, for instance with 60 grooves or recesses 42 is continuously capable of receiving up to 59 blood samples (it being recalled that one groove or recess 42 is always left free for the emergency blood sample operation in the described exemplary embodiment) and such 59 blood samples are held ready for analysis in the storage disc 15 and, on the other hand, since the mixing or mixer disc or disc means 17 which is driven independent of the storage disc 15, possesses the same blood sample take-up capacity, the blood samples which are accommodated to the control cycle or operating rate of the automatic blood analyzer, can either be delivered in a coherent sequence or in batches, and thus there is available a relatively large internal buffer capacity, and there is afforded an extremely great and hardly exhaustible flexibility as concerns the organization of the blood samples. The entire buffer capacity of the storage and mixing apparatus 180 is, of course, not limited in any way to the aforementioned 118 blood samples (2×59 blood samples) which have been merely indicated as an exemplary number and in is no way to be considered as placing any limitation upon the teachings and principles of the invention.

In keeping with the inventive teachings and principles there can be used pairings of storage discs and mixing discs containing an appreciably greater number of blood sample take-up grooves or recesses, such as the grooves or recesses 42 and 43 previously discussed and which, if desired, can be loaded by two blood sample loading devices, such as two of the loading devices or units 3 previously described, particularly in those instances where the operating cadence or rate of the automatic blood analyzer or analyzers should be very high.

Notwithstanding the possibility of providing an uninterrupted input sequence of the blood samples to be analyzed, there is still beneficially possible at any point in time in the operation of the storing and mixing apparatus 180 an overriding or momentary cutting-out of the analysis of the previously infed so-to-speak routine blood samples in favor of immediately accomplishing blood sample analysis of emergency blood samples. All of this renders possible a wide flexibility or variation in the operation of the storage and mixing apparatus 180 in such a manner that there can be effectively satisfied practically all external requirements as concerns organization of the delivery of the blood samples (routine or standard blood sample analysis or special blood sample analysis as in the case of an emergency situation or condition), the operating or working sequence of the blood sample analysis and as far as the equipment structure is concerned, the course or pattern of operation of the storage and mixing apparatus 180 which processes the blood samples to be analyzed. The proposed storage and mixing apparatus 180 and possible modifications thereof thus fulfill all of the requirements which are placed upon an interface between computable or predictable high automation requirements and a non-computable or non-predictable environment or surroundings.

A blood sample stoppered test-tube like container, such as the container or vessel 4a of FIG. 1, which contains either a blood sample 16 or an emergency blood sample 93 and which is manually delivered to the blood sample loading device or unit 3 is taken-over at the storage disc or disc means 15 in order to be either immediately delivered or transferred to the blood sample transfer location or position 5a, as is the case for an emergency blood sample 93, or according to a predeterminate operating sequence or pattern to the blood sample transfer location 5a as is the case for the routinely or standardly processed or analyzed blood samples 16 shown in FIG. 1. The blood sample stoppered test-tube like container 4a containing the blood sample 16 is transferred from the storage disc 15 which operates in the normal or routine operational mode in a stepwise or incrementally occurring storage operation to the continually occurring blood sample mixing mode by virtue of the continual rotation of the mixing disc 17 as heretofore described. The minimum mixing time for the blood samples, indicated by the blood samples 18 transferred to the mixing disc 17, is predetermined. After expiration of the contemplated blood sample mixing or moving time, then the blood sample, such as the blood samples 140, can be selectively rotated about the lengthwise axis of the associated stoppered test-tube like container of such blood sample 140 so that there can be read the blood identification data or marking. In so doing, there can be decided whether the identified blood sample should be evaluated or simply eliminated. By means of the blood sample removal or extraction device 7 there is removed a part of the blood from the stoppered test-tube like container housing the blood sample 140. For that purpose, the mixing disc or disc means 17 is brought to standstill. This blood sample removal or extraction operation is accomplished through the stoppered container or vessel in that the hollow needle or needle member 114 pierces the flexible stopper or rubber cap 141 (see FIG. 10).

Thereafter, the mixing or mixer disc 17 is again placed into operation. After each blood sample removal or extraction operation the hollow needle 114 is advantageously flushed or washed by means of a suitable flushing or washing solution or agent, and the thus cleansed hollow needle 114 is then ready for the next blood sample removal or extraction operation.

It is here also mentioned that there is effectively monitored the operation of the discs 15 and 17. Each passage of a groove or recess 42 for taking-up one of the test-tube like containers 4a of the blood samples and each disc revolution and each blood sample container transfer operation from the storage disc 15 to the mixing disc 17 is electronically stored. From such stored data there can be controlled the operation of both of the drive motors 33 and 36 for the discs 15 and 17, respectively, and the drive means 80, 58, 100, 128 and 132 for the loading device, transfer device, removal device and ejection devices. Moreover, in accordance with a further exemplary embodiment of the inventive apparatus the stored data of a blood sample identification can be used for the entire control operation.

Furthermore, the electronic control or control means receives data from the blood analysis device and from a manual control for controlling the speed of blood sample processing and the cycle time for the blood sample removal, on the one hand, and for the (manually-operated) switching over to an emergency blood sample analysis mode of operation, on the other hand. With the data for triggering the last-mentioned mode of operation there are activated operational procedures which are maintained separate from the normal mode of operation and from which there is automatically again switched over to the normal or routine operational mode.

If up to now there has been described an exemplary embodiment of storage and mixing apparatus where there has only been employed one only storage disc and one mixing disc, in other words two discs or disc means, it is to be understood and appreciated that modified constructions are readily possible and which use more than one storage disc. Such type of modified designs then can be desired and useful if, for instance, a predetermined batch of blood samples should be accommodated in the storage and mixing apparatus and whose number exceeds the number of grooves or recesses (less the one groove or recess provided for the emergency blood sample analysis) of the storage disc. In such case, there can be provided, and this is totally within the spirit and teachings of the invention, a storage operation and a mixing operation for blood samples which are accomplished independent of one another. This can be realized by a blood sample loading operation for blood sample containers or vessels and associated with the storage operation and by a removal operation for the blood samples which is associated with the mixing operation. Furthermore, in such event there is provided a blood sample transfer operation for transfer of the blood sample containers from the storage operation into the mixing operation or back again and which briefly connects with one another the storage operation and the mixing operation. For the storage operation, there is provided a first storage disc and a second storage disc which are functionally interconnected by a first transfer device and mixing disc by means of a second transfer device. The loading operation and the removal operation remain essentially as heretofore described.

It should be understood that based upon the teachings concerning the modified embodiment further groove discs can be incorporated into the apparatus, and such concerns equally storage discs and/or mixing discs. Between each two discs there is always provided a transfer device which in the case of a number of discs then conjointly renders possible a cascaded operation. The individual discs are driven independently of one another in order to fulfill the heretofore discussed communication requirements. In this connection, the discs which are not at the end of the arrangement, in other words the "non-terminal" discs, in contrast to the "terminal" discs possess axially continuous or throughpassing grooves or recesses. Yet, it is to be noted, that such axially continuous grooves also can be provided for the terminal discs.

The incorporation of additional discs and the joining together of a plurality of discs into a disc stack or pile affords an expanded flexibility in the operation which can be exploited for a continuous or continual operation. For instance, a part of the stack can be used for storage (such discs only move for accomplishing the loading-/transfer operation), the other part of the stack is used for mixing (these discs move continually). Now the flexibility resides in the fact that a storage disc can be converted from the storage operation into the mixing operation or, in a manner analogous thereto, a mixing disc can be converted from performing the mixing operation into the storage operation. In this way, the respective stack part which participates in storage of the blood samples and mixing of the blood samples can be varied and in point of fact there is thus realized an actually random stowing or storage of blood samples. Viewed in this manner, the apparatus possesses an "internal" buffer capacity which from the standpoint of the process technology can be optimumly utilized by appropriate operation of the apparatus. In this regard, the apparatus can operate in a two-disc operational mode in which the inner discs remain stationary and only participate in the transfer operation, whereas the terminal discs operate in the storage mode and in the mixing mode. As soon as there has been determined by a counting operation that the storage disc is about to be overfilled, then the neighboring disc functions as a storage disc and receives blood samples from the first storage disc. In the same manner, a mixing disc can be stopped and/or placed into the storage mode of operation whenever this is desired. This constitutes a further aspect of the previously discussed flexibility.

While there are shown and described present preferred embodiments of the invention, it is to be distinctly understood that the invention is not limited thereto, but may be otherwise variously embodied and practiced within the scope of the following claims. Accordingly,

What we claim is:

1. An apparatus for storing and mixing blood samples housed in containers for automatic analysis of the blood samples, comprising:
   at least one drivable storage disc for the storage of the blood samples;
   at least one mixing disc for preparing the blood samples;
   means for driving the at least one mixing disc independently of the at least one storage disc;
   said at least one storage disc and said at least one mixing disc being arranged adjacent one another in parallel planes;
   each of said discs being provided with groove means for receiving containers housing the blood samples; and
   a transfer device cooperating with said at least one storage disc and said at least one mixing disc for transfer of the containers housing the blood samples from the at least one storage disc to the at least one mixing disc.

2. The apparatus as defined in claim 1, wherein:
   each of said discs having a side including means for receiving the containers housing the blood samples;
   said side of said at least one storage disc confronting said side of said at least one mixing disc;
   said groove means of said at least one storage disc and said groove means of said at least one mixing disc respectively defining radial grooves at each side of each disc, which grooves extend to each disc edge;
   said radial grooves of said at least one storage disc and said radial grooves of said at least mixing disc complementing each other and each said radial groove serving for the reception of a container housing a blood sample;

a loading device for loading the containers housing the blood samples into the at least one storage disc; and a blood removal device for removing blood samples from the containers located in the at least one mixing disc and for delivery of the removed blood of the blood sample to a blood analyzer.

3. The apparatus as defined in claim 2, further including:

a blood analyzer operatively connected with said blood removal device for the reception of blood of the blood samples for blood analysis.

4. The apparatus as defined in claim 2, further including:

a code reading device for identifying a code applied to the container of each blood sample.

5. The apparatus as defined in claim 4, wherein:

said code reading device is arranged at the region of said blood removal device.

6. The apparatus as defined in claim 4, wherein:

said loading device comprises a threaded spindle drive means;

said threaded spindle drive means comprising a nut member;

said nut member conveying a container containing a blood sample into one of the groove means of the at least one storage disc; and said at least one storage disc being stationary during conveyance of the container with the blood sample into said groove means.

7. The apparatus as defined in claim 6, wherein:

said threaded spindle drive means includes a threaded spindle and a drive motor for said threaded spindle;

electronic control means provided for said drive motor for said threaded spindle;

said loading device being provided with light barrier means activatable by a container housing a blood sample which is placed into said loading device; and said light barrier means when activated by the inserted container housing the blood sample switching on the drive motor for the threaded spindle by means of the electronic control.

8. The apparatus as defined in claim 7, wherein:

said loading device comprises terminal switch means;

said terminal switch means being actuatable by said nut member of said threaded spindle upon departure of the container housing the blood sample from said loading device;

drive means for driving said at least one storage disc; and said terminal switch means turning on said drive motor for said at least one storage disc.

9. The apparatus as defined in claim 8, wherein:

said loading device comprises a screening cap which obturates towards the outside said loading device after having loaded a container housing a blood sample into the loading device.

10. The apparatus as defined in claim 9, wherein:

said transfer device comprises:

crank drive means; and plunger means operated by said crank drive means;

said plunger means being directed towards one of the groove means of said at least one storage disc and which contains a container housing a blood sample; and said crank drive means operating said plunger means in order to transfer the container having the blood sample from the groove means of the at least one storage disc into an oppositely situated groove means of the at least one mixing disc.

11. The apparatus as defined in claim 10, further including:

two electromagnets arranged at the region of the transfer device;

each of said groove means of said at least one storage disc and said at least one mixing disc being provided with clamp means for securing a container housing the blood sample in the associated groove means;

one of said two electromagnets serving for opening the clamp means of the groove means of the at least one storage disc; and the other of said at least two electromagnets serving for opening the clamp means of the groove means of the at least one mixing disc.

12. The apparatus as defined in claim 11, wherein:

said blood removal device comprises a rotating body member;

means for displacing said rotating body member for contact with a container housing the blood sample to establish a frictional connection between said rotating body member and said container;

said rotating body member serving for rotating the blood sample about a lengthwise axis thereof within the associated groove means;

said blood removal device further comprising a needle support which can be advanced toward the container housing the blood sample;

said container housing the blood sample having a piercable stopper;

a needle arranged at said needle support; and said needle piercing said pierceable stopper to enable removal of blood from the blood sample within the container.

13. The apparatus as defined in claim 12, further including:

a flushing device for conducting a flushing agent into the needle after removal of blood from the blood sample and after retraction of the needle support;

said needle comprising a lateral bore through which the flushing agent can escape out of the needle; and a flushing chamber for receiving flushing agent which has escaped out of the needle 14. The apparatus as defined in claim 12, further including:

sensor means for determining operation of said at least one storage disc and said at least one mixing disc.

15. The apparatus as defined in claim 14, wherein:

said sensor means comprises first sensor means for counting the groove means of said discs; and said sensor means further comprising second sensor means for counting the number of revolutions of said discs.

16. The apparatus as defined in claim 15, wherein:

each said first sensor means and said second means comprise light barrier means.

17. The apparatus as defined in claim 16, further including:

means defining an ejection location for the containers housing the blood samples; and said means defining an ejection location comprising an electromagnet provided at the region of said at least one mixing disc for opening the clamp means for the containers located in the groove means of said at least one mixing disc.

18. The apparatus as defined in claim 17 wherein:
said means defining said ejection location defines an ejection position for emergency blood samples;
said ejection position for emergency blood samples being provided with electromagnet means for opening the clamp means of containers having emergency blood samples.

19. The apparatus as defined in claim 18, further including:
receptacle means for collecting containers housing blood samples which have been identified;
receptacle means for collecting containers housing blood samples which have not been identified; and
receptacle means for collecting containers housing blood samples constituting emergency blood samples.

20. The apparatus as defined in claim 1, further including:
support means for supporting said at least one storage disc and said at least one mixing disc; and
said at least one storage disc and said at least one mixing disc are arranged substantially vertically with respect to said support means.

21. The apparatus as defined in claim 1, wherein:
said at least one storage disc and said at least one mixing disc are arranged at an inclination with respect to the line of action of the force of gravity.

22. The apparatus as defined in claim 1, wherein:
each of said at least one storage disc and said at least one mixing disc have essentially the same diameter; and
said at least one storage disc and said at least one mixing disc being substantially coaxially arranged.

23. The apparatus as defined in claim 22, wherein:
said at least one storage disc has a predetermined number of said groove means:
said at least one mixing disc has a predetermined number of groove means; and
said predetermined number of groove means of said at least one storage disc and said predetermined number of groove means of said at least one mixing disc being the same.

24. An apparatus as described in claim 1, further including closed containers for storing and mixing blood samples.

25. An apparatus for storage and moving blood samples for automatic analysis of the blood samples, comprising:
storage disc means for the storage of the blood samples;
means for selectively moving said storage disc means;
mixing disc means for preparing the blood samples;
means for driving the mixing disc means independently of the storage disc means;
said storage disc means and said mixing disc means being positioned in coacting relationship to one another, wherein the storage disc means and mixing disc means are arranged adjacent one another in parallel planes;
each of said disc means being provided with means for receiving containers housing the blood samples; and
transfer means cooperating with said storage disc means and said mixing disc means for transfer of the containers housing the blood samples from the storage disc means to the mixing disc means.

26. A method of handling blood samples for the automatic analysis of the blood sample, comprising the steps of:
loading stoppered containers housing blood samples to a storage means at which there are stored the containers housing the blood samples;
transferring the containers housing the blood samples from the storage means to a mixing means operated independently of the storage means;
mixing the blood samples housed in the containers in the mixing means; and
removing blood of the blood samples housed in the containers located at the mixing means;
wherein the method further includes the steps of:
using as the storage means a storage disc having receiving grooves for the containers housing the blood samples;
conveying the containers housing the blood sample in a predetermined sequence to a transfer location containing a transfer means for transferring the containers housing the blood samples from the storage disc to a mixing disc of the mixing means, with the storage disc and the mixing disc being arranged adjacent one another in parallel planes;
the transfer means transferring the containers housing the blood samples from the storage disc to the mixing disc;
mixing the containers housing the blood samples for a predetermined mixing time at the mixing disc; and
removing a part of the blood from at least predetermined ones of the containers housing the blood samples by means of a blood removal device.

27. The method as defined in claim 26, further including the steps of:
rotating each container from which there is to be removed a part of the blood of the blood sample about a lengthwise axis of the associated container prior to removal of part of the blood of the blood sample from the container; and
simultaneous with said rotation reading blood sample identification data provided at the container.

28. The method as defined in claim 27, further including the step of:
utilizing the blood sample identification data for determining whether the identified blood sample is to be evaluated or rejected.

29. The method as defined in claim 26, further comprising the step of:
leaving an empty position at the storage disc and an empty position at the mixing disc, wherein these two empty positions are left empty for the reception of a container housing an emergency blood sample.

30. The method as defined in claim 29, further including the steps of:
upon emergency analysis of the emergency blood sample using said two empty positions;
overriding routine operation of the storage disc and the mixing disc;
placing the empty position of the storage disc at the location of a loading position for loading a container having an emergency blood sample therein;
moving the empty position of the mixing disc to the transfer location;
conveying the container having the emergency blood sample and located in the empty position of the storage disc immediately to the transfer location;

displacing the container housing the emergency blood sample from the storage disc into the empty position of the mixing disc; and directly delivering the container housing the emergency blood sample from the transfer position and without any mixing movement of the mixing disc, directly to the location of a blood removal device for removal of a part of the blood of the emergency blood sample for analysis.

31. The method as defined in claim 26, further including the steps of:

depositing the containers housing the blood samples in different separate receptacles in order to physically separate said containers from one another.

32. The method as defined in claim 26, further including the step of:

after each removal of part of the blood from a container housing the blood sample washing with a flushing agent parts of a blood removal device which have come into contact with the removed blood of the blood sample.

33. The method as defined in claim 26, further including the steps of:

monitoring operation of the discs;

said monitoring step comprising electronically storing each passage of a groove for receiving a container housing a blood sample during each revolution of each of said discs;

said monitoring step further comprising electronically storing as stored data the transfer of each container housing the blood samples from the storage disc to the mixing disc; and deriving from the stored data a predetermined operation of two drive motors for respectively driving the storage disc and the mixing disc and for controlling drive means for a loading device, said transfer means, a removal device and an ejection device.

34. The method as defined in claim 26, further including the steps of:

incorporating additional discs so as to form a disc stack; and employing a part of the disc stack for storage of the disc stack for mixing of the blood samples in the containers.

35. The method as defined in claim 34, further including the steps of:

selectively altering the operation of the storage disc from a storage operation to a mixing operation or the operation of the mixing disc from a mixing operation to a storage operation.

36. The method as defined in claim 35, further including the steps of:

variably retaining part of the disc stack for a respective storage operation and mixing operation in order to accommodate the storing of the containers housing the blood samples as a function of the available supply of blood samples.

37. The method as defined in claim 34, further including the steps of:

controlling the disc stack to operate in a two-disc mode, wherein inner discs of the disc stack are stationary and only participate in a transfer of the containers housing the blood samples and terminal discs of the disc stack operate in a storage mode and in a mixing mode.

38. The method as defined in claim 34, further including the steps of:

filling the storage disc defining a first storage disc with a predetermined number of containers;

following filling of said storage disc with said predetermined number of containers a neighboring disc, viewed in the direction of a mixing disc, functions as a storage disc for taking over containers housing the blood sample from the first storage disc.

39. An apparatus for storing and mixing blood samples housed in containers for automatic analysis of the blood samples, comprising:

at least one drivable storage disc for the storage of the blood samples;

at least one mixing disc for preparing the blood samples;

means for driving the at least one mixing disc independently of the at least one storage disc;

said at least one storage disc and said at least one mixing disc being arranged adjacent one another;

each of said discs being provided with groove means for receiving containers housing the blood samples in radially-positioned tubes, whereby upon positioning said tubes in said grooves, an axis of each of said tubes lies along a radius of said discs; and, a transfer device cooperating with said at least one storage disc and said at least one mixing disc for transfer of the containers housing the blood samples from the at least one storage disc to the at least one mixing disc.

* * * * *